United States Patent
Griswold et al.

(10) Patent No.: US 7,976,951 B2
(45) Date of Patent: *Jul. 12, 2011

(54) LAMINATE CONTAINING AN ADHESIVE-FORMING COMPOSITION

(75) Inventors: Roy M. Griswold, Ballston Spa, NY (US); Robert L. Frye, Concord, OH (US); Mark J. Bisaillon, Saratoga Springs, NY (US)

(73) Assignee: Momentive Performance Materials Inc., Albany, NY (US)

( * ) Notice: Subject to any disclaimer, the term of this patent is extended or adjusted under 35 U.S.C. 154(b) by 75 days.

This patent is subject to a terminal disclaimer.

(21) Appl. No.: 12/466,727

(22) Filed: May 15, 2009

(65) Prior Publication Data

US 2009/0311459 A1   Dec. 17, 2009

Related U.S. Application Data

(63) Continuation-in-part of application No. 11/598,925, filed on Nov. 14, 2006, now Pat. No. 7,829,116.

(51) Int. Cl.
 *B32B 27/40* (2006.01)
(52) U.S. Cl. ............. 428/423.1; 428/424.2; 428/424.4; 428/446; 428/448; 428/473.5; 428/480; 428/500; 428/523; 525/455; 525/456; 525/457; 525/100; 525/104; 525/106; 525/477
(58) Field of Classification Search .................. None
See application file for complete search history.

(56) References Cited

U.S. PATENT DOCUMENTS

| | | | |
|---|---|---|---|
| 3,627,722 A | 12/1971 | Seiter | |
| 3,632,557 A | 1/1972 | Brode et al. | |
| 3,979,344 A | 9/1976 | Bryant et al. | |
| 4,222,925 A | 9/1980 | Bryant et al. | |
| 4,470,962 A | 9/1984 | Keith et al. | |
| 4,655,767 A | 4/1987 | Woodard et al. | |
| 4,668,232 A | 5/1987 | Cordes et al. | |
| 4,837,274 A | 6/1989 | Kawakubo et al. | |
| 4,900,772 A | 2/1990 | Imanaka et al. | |
| 4,904,732 A | 2/1990 | Iwahara et al. | |
| 5,223,575 A | 6/1993 | Mori et al. | |
| 5,338,490 A | 8/1994 | Dietz et al. | |
| 5,556,636 A | 9/1996 | Yano et al. | |
| 5,660,178 A | 8/1997 | Kantner et al. | |
| 5,725,947 A | 3/1998 | Johannsen et al. | |
| 5,750,136 A | 5/1998 | Scholz et al. | |
| 5,767,197 A | 6/1998 | Fukatsu et al. | |
| 6,121,354 A | 9/2000 | Chronister | |
| 6,133,395 A | 10/2000 | Miyata et al. | |
| 6,562,363 B1 | 5/2003 | Mantelle et al. | |
| 6,746,689 B2 | 6/2004 | Fischer et al. | |
| 6,803,412 B2 | 10/2004 | Nguyen-Misra et al. | |
| 6,858,997 B1 | 2/2005 | Poindexter | |
| 6,884,852 B1 | 4/2005 | Klauck et al. | |
| 6,936,661 B2 | 8/2005 | Koch et al. | |
| 7,405,259 B2 | 7/2008 | Frye et al. | |
| 2003/0221770 A1 * | 12/2003 | Meixner et al. | ............... 156/230 |
| 2005/0019385 A1 | 1/2005 | Houze | |
| 2005/0282977 A1 | 12/2005 | Stempel et al. | |
| 2006/0078601 A1 | 4/2006 | Kanios et al. | |
| 2006/0078603 A1 | 4/2006 | Nguyen | |
| 2006/0247370 A1 | 11/2006 | Frye et al. | |

FOREIGN PATENT DOCUMENTS

| | | |
|---|---|---|
| JP | 56-082863 | 7/1981 |
| JP | 57-207663 | 12/1982 |
| JP | 59-172575 | 9/1984 |
| JP | 59-174672 | 10/1984 |
| JP | 61-047774 | 3/1986 |
| JP | 61-218631 | 9/1986 |
| JP | 61-218672 | 9/1986 |
| JP | 61-218673 | 9/1986 |
| JP | 62-057478 | 3/1987 |
| JP | 62-057479 | 3/1987 |
| JP | 62-057480 | 3/1987 |
| JP | 62-089782 | 4/1987 |
| JP | 03-259981 | 11/1991 |
| JP | 09-165565 | 6/1997 |
| WO | WO 2004/094549 | 11/2004 |

OTHER PUBLICATIONS

"Characterization of Hydroxyl-terminated Polybutadiene" authored by Villar et al. and published in Polymer Bulletin (1995) 35, 481-488.*

* cited by examiner

Primary Examiner — Marc S Zimmer
(74) Attorney, Agent, or Firm — Dominick G. Vicari; Joseph S. Ostroff; Wiggin and Dana LLP

(57) ABSTRACT

A laminate includes a backing material coated with an adhesive composition. The adhesive composition includes a silylated polyurethane obtained from the silylation of a polyurethane prepolymer derived from the reaction of polybutadiene polyol and polyisocyanate; and an additional adhesive component.

20 Claims, 1 Drawing Sheet

LAMINATE CONTAINING AN ADHESIVE-FORMING COMPOSITION

CROSS REFERENCE TO RELATED APPLICATIONS

Figure 1:
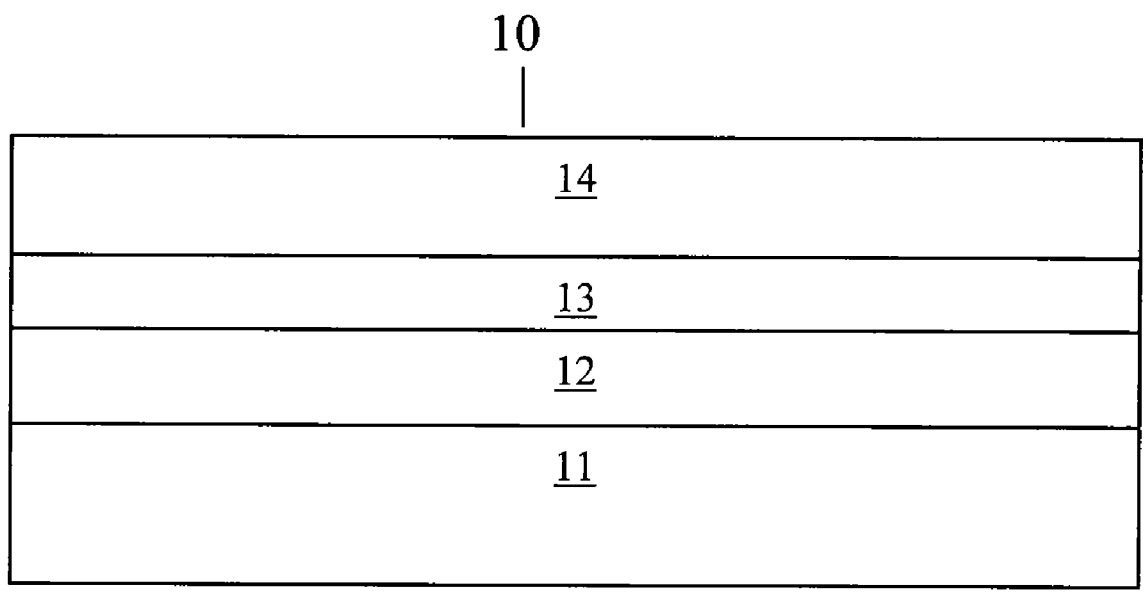

The present application is a continuation-in-part of U.S. application Ser. No. 11/598,925, filed Nov. 14, 2006, now U.S. Pat. No. 7,829,116, to which entitlement to priority is claimed and the disclosure of which is incorporated herein by reference in its entirety.

FIELD OF THE INVENTION

This invention relates to laminates comprising a backing material coated with cured adhesives, and to methods of making and employing the laminates.

BACKGROUND OF THE INVENTION

Adhesives are typically blended with other non-adhesive polymers or with adhesives to alter the final pressure sensitive adhesive properties such as re-positionability, adhesion to various surfaces, and control of drug agent delivery rates. Typically these encompass compositions where acrylic and silicone pressure sensitive adhesives, or other organic and silicone adhesives are blended.

Blended adhesive compositions are known in the art.

U.S. Pat. No. 5,725,947 describes a film composite wherein a first adhesive is an acrylic latex and a heat-activated urethane latex, a second adhesive is applied over the first yielding a re-positionable composite that upon extended contact builds adhesion.

U.S. Pat. No. 5,338,490 describes ionically conductive hydrophilic adhesive as a continuous phase and a hydrophobic adhesive discontinuous phase for biomedical applications.

Published U.S. Patent Application No. 2005/0282977 describes silicone pressure sensitive adhesive and silicone gel blend for skin-attachable use.

WO 2004094549 describes compositions wherein two adhesives, one with acidic functionality then other basic functionality, are blended then crosslinked.

Several transdermal patent applications exist wherein the active agent is incorporated into compositions of polymeric and/or pressure sensitive adhesives. Illustrative of these are the following:

Published U.S. Patent Application No. 20060078603 describes blends of acrylic adhesives with acrylic or rubber-based adhesives to provide desired drug flux in transdermal systems.

Published U.S. Patent Application No. 20050019385 describes blending low and high silanol concentration silicone pressure sensitive adhesives.

Published U.S. Patent Application No. 20060078601 describes acrylic-based adhesives with a second polymer selected from silicone, rubber, polyurethane, polyisobutylene, polyvinyl ethers, styrene block copolymers, polyether block copolymers, ethylene/vinyl acetate, vinyl acetate adhesives, polyvinylypyrrolidones and bio-adhesives.

Despite the disclosures contained in the above-described art, a need still exists for new forms of blended adhesive compositions providing good peel adhesion to a wide variety of surfaces, including flexible and rigid substrates.

SUMMARY OF THE INVENTION

In accordance with the present invention, there is provided a laminate comprising a backing material having an adhesive composition applied thereto, the adhesive composition including (a) a silylated polyurethane prepolymer, the silylated polyurethane prepolymer being obtained from the silylation of a polyurethane prepolymer derived from the reaction of at least one polybutadiene polyol with at least one polyisocyanate; and, (b) an additional adhesive component other than the silylated polyurethane prepolymer (a).

In accordance with another aspect of the invention, there is provided a method for making a laminate comprising the steps of: (a) providing an adhesive composition including (i) a silylated polyurethane prepolymer, said polyurethane prepolymer being obtained from the silylation of a polyurethane prepolymer derived from the reaction of at least one polybutadiene polyol with at least one polyisocyanate; and (ii) an additional adhesive component other than component (i); (b) applying said adhesive composition to a backing material; and (c) curing the adhesive composition to provide an adhesive layer, thereby making the laminate.

In accordance with another aspect of the invention, there is provided a method of applying a laminate to a surface of a substrate comprising the steps of: (a) providing a laminate comprising a backing material with a layer of a cured adhesive composition in contact with at least one side of the backing material, the laminate having a release liner disposed on the layer of the cured adhesive composition, the cured adhesive composition being prepared by curing an admixture of (i) a silylated polyurethane prepolymer, said silylated polyurethane prepolymer being obtained from the silylation of a polyurethane prepolymer derived from the reaction of at least one polybutadiene polyol with at least one polyisocyanate; and (ii) an additional adhesive component other than component (i); (b) removing the release liner; and (c) applying the laminate to the surface of the substrate such that the layer of the adhesive composition of the laminate contacts and adheres to the surface of the substrate.

The laminates of the present invention provide improved peel adhesion to various substrates including the surfaces of aircraft components, motor vehicles, buildings, machinery, various types of equipment or tools and skin.

BRIEF DESCRIPTION OF THE DRAWING(S)

FIG. 1 is a diagrammatic illustration of a laminate structure of the invention.

DETAILED DESCRIPTION OF THE INVENTION

The present invention is directed to a laminate comprising a backing material having an adhesive composition applied thereto. The adhesive composition includes (i) a silylated polyurethane prepolymer, the silylated polyurethane prepolymer being obtained from the silylation of a polyurethane prepolymer derived from the reaction of at least one polybutadiene polyol with at least one polyisocyanate; and, (ii) an additional adhesive component other than the silylated polyurethane prepolymer (i). In one embodiment, the adhesive composition coated on the backing material is a cured composition.

The polyurethane prepolymer of the present invention is derived from the reaction of at least one polybutadiene polyol with at least one polyisocyanate. The polybutadiene polyols useful for preparing the isocyanate-terminated and hydroxyl-terminated polyurethane prepolymers are those possessing a number average molecular weight (Mn) of from about 500 to about 10,000, and advantageously from about 800 to about 5,000, a primary hydroxyl group content of from about 0.1 to about 2.0 meq/g, and advantageously from about 0.3 to about 1.8 meq/g, a degree of hydrogenation of from 0 up to 100 percent of the olefinic sites present and an average content of copolymerized additional monomer(s) of from 0 up to about 50 weight percent.

Hydroxyl-terminated butadienes of the above-described type, averaging more than one predominantly primary hydroxyl group per molecule, e.g., averaging from about 1.7 to about 3 or more primary hydroxyl groups per molecule, are suitably employed herein. The hydroxyl-terminated polybutadienes will possess an average of at least about 2, and advantageously from about 2.4 up to about 2.8, hydroxyl groups per molecule, the hydroxyl groups being predominantly in terminal allylic positions on the main, i.e., generally longest, hydrocarbon chain of the molecule. By "allylic" configuration is meant that the alpha-allylic grouping of allylic alcohol, i.e., the terminal hydroxyl groups of the polymer, are bonded to carbon atoms adjacent to double bonded carbon atoms.

The ratio of cis-1,4, trans-1,4 and 1,2-vinyl unsaturation which occurs in the butadiene polymers employed in this invention, the number and location of the hydroxyl groups and the molecular weight of the butadiene polymers will be influenced by the process employed for their manufacture, the details of which are known in the art.

Hydroxyl-terminated polybutadienes having unsaturation and those hydrogenated to yield saturated hydroxyl-terminated polybutadienes possessing these characteristics are commercially available from several sources and are therefore conveniently employed herein.

The useful hydroxyl-terminated polybutadienes herein can also incorporate one or more other copolymerizable monomers which can confer particularly desirable properties upon the silylated polymers herein and the pressure sensitive adhesive compositions prepared therewith. The total amount of copolymerized monomer will not exceed, on average, 50 weight percent of the hydroxyl-terminated polybutadiene copolymer. Included among the copolymerizable monomers are monoolefins and dienes such as ethylene, propylene, 1-butene, isoprene, chloroprene, 2,3-methyl-1,3-butadiene, 1,4-pentadiene, etc., and, ethylenically unsaturated monomers such as acrylonitrile, methacrylonitrile, methylstyrene, methyl acrylate, methyl methacrylate, vinyl acetate, etc. Alternatively or in addition thereto, the hydroxyl-terminated polybutadienes can be reacted with one or more other monomers to provide hydroxyl-terminated block copolymers. Such monomers include 1,2-epoxides such as ethylene oxide and propylene oxide which will provide polyether segments, e-caprolactone which will provide polyester segments, and the like.

The polybutadiene-based polyurethane prepolymer is obtained by reacting one or more hydroxyl-terminated, optionally hydrogenated, linear or branched polybutadiene homopolymers or copolymers with an organic polyisocyanate, e.g., an organic diisocyanate, optionally together with one or more other difunctional compounds and/or hydroxyl-terminated polymers, to provide (1) an isocyanate-terminated polyurethane prepolymer when the total equivalents of isocyanate functionality exceeds the total equivalents of hydroxyl functionality, and (2) a hydroxyl-terminated polyurethane prepolymer when the total equivalents of hydroxyl functionality exceeds the total equivalents of isocyanate functionality.

Methods of preparing polyurethane prepolymers, and silylated polyurethane prepolymers are well known in the art. See, e.g., U.S. Pat. Nos. 3,627,722, 3,632,557, 3,979,344, and 4,222,925, which are incorporated herein by reference.

The prepolymer is made by reacting a hydroxy-terminated polymeric material with an isocyanate to provide a prepolymer chain having NCO and/or OH groups at the ends thereof. The resulting polyurethane prepolymer is then reacted with a sufficient amount of a silane end-capper to provide silylated polyurethane prepolymer.

The isocyanates that are reacted with the polyurethane prepolymers of the present invention are organic isocyanates and include any of the known and conventional organic polyisocyanates, especially organic diisocyanates, from which polyurethane polymers have heretofore been prepared. Useful diisocyanates include, for example, 2,4-toluene diisocyanate, 2,6-toluene diisocyanate, 4,4' diphenyl-methanediisocyanate, isophorone diisocyanate, dicyclohexylmethane-4, 4'-diisocyanate, various liquid diphenylmethanediisocyantes containing a mixture of 2,4- and 4,4' isomers, Desmodur N® (Bayer) and the like, and mixtures thereof. Isophorone diisocyanate is especially advantageous for use in preparing the polyurethane prepolymers herein.

The polyurethane prepolymer may be prepared by mixing the hydroxy-terminated polymer and organic isocyanate together at ambient temperature and pressure, although the speed of the reaction is significantly increased if the temperature of the reaction mixture is raised to a higher temperature, for example, a temperature between 60-100° C. A molar ratio of NCO to OH from about 1.1 to about 4.0, depending on the selection of the particular hydroxyl-terminated polybutadiene polyol, is used to provide isocyanate-terminated polyurethane prepolymers. A molar ratio of NCO to OH from about 0.3 to about 0.95, and more preferably from about 0.5 to about 0.90, depending on the specific hydroxyl-terminated polybutadiene polyol, is used to provide hydroxyl group-terminated polyurethane prepolymers.

Silylation of the isocyanate-terminated polyurethane prepolymer described herein can be accomplished by reacting the prepolymer with a silane possessing at least one hydrolyzable group and at least one functionality which is reactive for isocyanate, i.e., an active hydrogen-containing group such as hydroxyl, carboxylic acid, mercapto, primary amino or secondary amino. Advantageously, the silane is a primary or secondary aminosilane of the general formula:

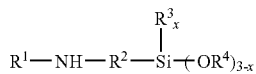

wherein $R^1$ is hydrogen or an alkyl group of from 1 to 10 carbon atoms, $R^2$ is a divalent alkylene group of from 3 to 10 carbon atoms, $R^3$ and $R^4$ each independently is an alkyl group of from 1 to 6 carbon atoms or an aryl group of from 6 to 8 carbon atoms, and x has a value of 0, 1 or 2.

Examples of aminosilanes for use in the silylation procedure herein are 3-aminopropyltrimethoxysilane, 3-aminopropyltriethoxysilane, 4-amino-3,3-dimethylbutyltrimethoxysilane, 4-amino-3,3-dimethylbutyldimethoxymethylsilane, N-methyl-3-amino-2-methylpropyltrimethoxysilane, N-ethyl-3-amino-2-methylpropyltrimethoxysilane, N-ethyl-3-amino-2-methylpropyldiethoxymethylsilane, N-ethyl-3-amino-2-methylpropyltriethoxy silane, N-ethyl-3-amino-2-methylpropylmethyldimethoxysilane, N-butyl-3-amino-2-methylpropyltrimethoxysilane, 3 (N-methyl-2-amino-1-methyl-1-ethoxy)-propyltrimethoxysilane, N-ethyl-4-amino-3,3-dimethylbutyldimethoxy-methylsilane and N-ethyl-4-amino-3,3-dimethylbutyltrimethoxysilane trimethoxysilane, and the like.

For applications such as use in sealant and coating compositions, the polyurethane prepolymers can be substantially fully silylated, i.e., all, or substantially all, of the isocyanate groups can be reacted with silane to provide a completely silylated polyurethane polymer.

However, where the silylated polyurethane polymer is to be incorporated into pressure sensitive adhesive compositions, it is important that the silylation be conducted to less than completion in order that the extent of crosslinking that occurs on subsequent cure of the silylated polymer not be so great as to adversely affect, and even eliminate, the pressure sensitive adhesive characteristics of the crosslinked polymer.

In conducting a partial silylation reaction, it can be useful to include a primary monoamine such as N-ethylbutylamine or similar capping reactant together with the silane as the amine will readily end-cap isocyanate groups thereby precluding them from reacting with the silane. The optimal amounts of silane and optional amine for achieving this less-than-complete silylation operation can be readily determined for a given isocyanate-terminated prepolymer employing known and conventional experimental techniques. Silylation of not more than about 95 percent, and advantageously not more than about 90 percent, of the total isocyanate groups present in the prepolymer is generally suitable for most pressure sensitive adhesive applications.

Silylation of the hydroxyl-terminated polyurethane prepolymer described herein can be accomplished by reacting the prepolymer with an isocyanatosilane. Suitable isocyanatosilanes are those of the general formula:

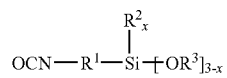

wherein $R^1$ is a divalent alkylene group of from 3 to 10 carbon atoms, $R^2$ and $R^3$ each independently is an alkyl group of from 1 to 6 carbon atoms or an aryl group of from 6 to 8 carbon atoms, and x has a value of 0, 1 or 2.

Examples of such isocyanatosilanes for use in the silylation procedure are λ-isocyanatopropyltrimethoxysilane, λ-isocyanatopropyltriethoxy-silane, λ-isocyanatomethylpropyltrimethoxysilane, λ-isocyanatomethylpropyltriethoxysilane, λ-isocyanatopropylmethyldimethoxysilane, λ-isocyanatopropyldimethylmethoxysilane and λ-isocyanatomethylpropyldimethylmethoxysilane, and the like.

As in the case of the silylated isocyanate-terminated polyurethanes described above, the silylation of the hydroxyl-terminated polyurethane prepolymers herein will be substantially complete, i.e., essentially no hydroxyl groups will be present following silylation, where the silylated polymers are to be incorporated in such products as sealants and coatings. However, silylation will be incomplete, or partial, where the silylated polymers are to be incorporated in pressure sensitive adhesive compositions. In the case of incomplete silylation, levels of silylation of not more than about 95 percent, and advantageously, not more than about 90 percent, of the total hydroxyl groups present in the prepolymer is generally suitable and can be achieved by appropriate adjustment of the amounts of isocyanatosilane being reacted for a given prepolymer.

In order to facilitate control over the extent of incomplete silylation, it may be advantageous to include a hydroxyl-reactive monofunctional reactant with the isocyanatosilane. Suitable reactants for this purpose include monoisocyanates such as n-butylisocyanate. These and similar reactants serve to cap some of the hydroxyl groups of the prepolymer preventing them from undergoing silylation. Amounts of such hydroxyl-reactive monomeric reactants and isocyanatosilanes that can be utilized for partial silylation herein can be readily determined for a specific hydroxyl-terminated polyurethane prepolymer employing routine experimental testing.

Adhesive components suitable for blending with the silylated prepolymer to form adhesive compositions of the invention include the types of adhesives that will be readily apparent to one skilled in the art. Such adhesive components include pre-formed adhesive materials that can be, e.g., conventional non-silicone adhesives, such as, commercial non-silicone adhesives that include compositions segmented by the type of base polymer; e.g., natural rubber, styrene butadiene rubber (SBR), styrene isoprene styrene (SIS), acrylic, isoprene, polyurethanes, and the like. Other pre-formed adhesives contemplated herein include conventional silicone adhesives, such as, commercial adhesives grouped into methyl, low phenyl, high phenyl silicones and the like.

In one embodiment of the invention, the pre-formed adhesives used for blending with the silylated prepolymer include, polyurethanes; acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tertbutylacrylamide, itaconic acid, vinylacetate, N-branched alkyl maleamic acids wherein the alkyl group has 10 to 24 carbon atoms, glycol diacrylates, or mixtures of these; natural or synthetic rubbers such as styrenebutadiene, butylether, neoprene, polyisobutylene, polybutadiene, and polyisoprene; polyvinylacetate; ureaformaldehyde resins; phenolformaldehyde resins; resorcinol formaldehyde resins, cellulose derivatives such as ethyl cellulose, methyl cellulose, nitrocellulose, cellulose acetatebutyrate, and carboxymethyl cellulose; and natural gums such as guar, acacia, pectins, starch, dextrin, albumin, gelatin, casein, etc. The pre-formed adhesives may be compounded with tackifiers and stabilizers as is well known in the art.

Other additional pre-formed adhesives usable in accordance with the invention include, e.g., silicone elastomers based on monomers of silanes, halosilanes, or $C_1$-$C_{18}$ alkoxysilanes, especially polydimethylsiloxanes which may be used alone or formulated with a silicone tackifier or silicone plasticizer which are selected from medically acceptable silicone fluids, i.e. non-elastomeric silicones based on silanes, halosilanes or $C_1$-$C_{18}$ alkoxysilanes. Typical silicone adhesives are available from Momentive Performance Materials-Silicones, e.g., Silgrip®.

The pressure sensitive adhesive compositions of the present invention can contain one or more chain extenders and/or one or more other polyols. Examples of suitable chain extenders are polyhydric alcohols such as ethylene glycol, propylene glycol, propane-1,3-diol, butane-1,4-diol, hexane-1,6-diol, diethylene glycol, triethylene glycol, tetraethylene glycol, dipropylene glycol, triethylene glycol, tetrathylene glycol, dipropylene glycol, tripropylene glycol, tetrapropylene glycol and the like. Additional polyols include polyether polyols, polyester polyols, polyetherester polyols, polyesterether polyols, polybutadienediols, polyoxyalkylene diols, polyoxyalkylene triols, polytetramethylene glycols, polycaprolactone diols and triols, and the like, all of which possess at least two primary hydroxyl groups.

Suitable catalysts useful in the preparation of the polyurethane prepolymers are known in the art, e.g., organoamine and organotin catalysts. Suitable catalysts include dialkyltin dicarboxylates such as dibutyltin dilaurate and dibutyltin acetate, tertiary amines, the stannous salts of carboxylic acids such as stannous octoate and stannous acetate, and the like.

Pressure sensitive adhesive compositions of the present invention possess superior adhesive and cohesive properties and can be obtained with the partially silylated polyurethanes described above. In addition to the partially silylated polyurethanes, a pressure sensitive adhesive composition in accordance with the invention will typically include one or more additives such as fillers, tackifiers, silane adhesion promoters, plasticizers, solvents, thixotropic agents, U.V. stabilizers, antioxidants, cure catalysts, etc., in the usual amounts.

Typical fillers suitable for addition to the pressure-sensitive adhesive compositions of this invention include fumed silica, precipitated silica and calcium carbonates. Treated calcium carbonates having particle sizes from about 0.07 µm to about 4 µm are particularly useful and are available under several trade names: Ultra Pflex®, Super Pflex®, Hi Pflex® from Specialty in Minerals; Winnofil® SPM, SPT from Zeneca Resins; Hubercarb® lat, Hubercarb® 3Qt and Hubercarb® W from Huber and Kotomite® from ECC. These fillers can be used either alone or in combination. The fillers can comprise up to about 200 parts per 100 parts of the silylated polymer component(s) with from about 80 to about 150 parts filler per 100 parts polymer being suitable for many adhesive applications.

The pressure sensitive adhesive composition of the present invention can contain from about 20 to about 60 parts, and advantageously from about 30 to about 50 parts, of one or more known of conventional tackifiers per 100 parts of silylated polyurethane polymer. Examples of suitable tackifiers are MQ silicone resins (for which a curing catalyst such as benzoyl peroxide will ordinarily be included), terpene oligomers, coumarone/indene resins, aliphatic, petrochemical resins, and modified phenolic resins.

Silane adhesion promoters can be employed at levels of from about 0.5 to about 5 parts per hundred parts of the silylated polyurethane polymer with from about 0.8 to about 1.5 parts per hundred parts polymer being especially advantageous. Suitable adhesion promoters include Silquest® A-1120 silane, Silquest A-2120 silane, Silquest® A-1170 silane and Silquest® A-187 silane, all of which are available from Momentive Performance Materials-Silicones.

Exemplary plasticizers include phthalates, dipropylene and diethylene glycol dibenzoates and mixtures thereof, epoxidized soybean oil, and the like. Dioctyl and diisodecylphthalate are commercially available under the trade names Jayflex® DOP and JayFlex® DIDP from Exxon Chemical. The dibenzoates are available as Benzoflex® 9-88, Benzoflex® 50 and Benzoflex® 400 from Velsicol Chemical Corporation. Epoxidized soybean oil is available from Houghton Chemical Corporation as Flexol® EPO. The plasticizer can comprise up to about 100 parts of the silylated polyurethane polymer with from about 40 to about 80 parts per hundred parts of silylated polymer being satisfactory in many cases.

Useful solvents include aromatic, aliphatic and esters ranging in amounts of from about 25 to about 75 per hundred parts by weight of silylated polyurethane prepolymer.

Illustrative of useful thixotropic agents are various castor waxes, fumed silica, treated clays and polyamides. These additives typically comprise about 1 to about 10 parts per hundred parts of silylated polyurethane prepolymer with from about 1 to about 6 parts being useful for most applications. The thixotropes include those available as: Aerosil® from Degussa, Cabo-Sil® TS 720 from Cabot, Castorwax® from CasChem, Thixatrol® and Thixcin® from Rheox and Dislon® from King Industries. If the thixotrope is reactive with silane (e.g., silica), adjustments to the amount formulated may be needed to compensate therefor.

U. V. stabilizers and/or antioxidants can be incorporated into the pressure sensitive adhesive compositions of this invention in an amount of from 0 to about 5 parts per hundred parts silylated polyurethane polymer with from about 0.5 to about 2 parts providing generally good results. These materials are available from Ciba-Geigy under the trade names Tinuvin® 770, Tinuvin® 327, Tinuvin® 213, Tinuvin® 622 and Irganox® 1010.

Suitable cure catalysts are the same as those previously described for preparation of the silylated polyurethane polymers. The catalysts typically compromise from about 0.01 to about 3 parts per hundred parts polymer with from about 0.01 to about 1.0 parts per hundred parts of polymer being entirely suitable in many cases.

The pressure sensitive adhesive compositions of the invention can be cured by exposure to moisture. Curing conditions typically include ambient temperature, e.g., about 23° C. and 50% relative humidity for 3 days and 37° C. and 95% relative humidity for another 4 days. Alternatively water can be mixed with an appropriate solvent such as isopropanol followed by mixing with the adhesive composition and coated, cured in conventional adhesive cure ovens known in the art.

The pressure sensitive adhesive compositions of the present invention can optionally further comprise from about 20% to about 70% by weight, preferably from about 0% to about 60% by weight, and most preferably from 40% to about 50% by weight of an organic solvent. Suitable organic solvents include any of the solvents conventionally used with organsiloxanes and have a boiling point below approximately 250° C., such as aromatic hydrocarbons, e.g., benzene, toluene and xylene; aliphatic hydrocarbons such as hexane, heptane, and cyclohexane; halogenated hydrocarbon solvents such as trichloroethane and chloroform; naphthas such as petroleum ether, and oxygenated solvents such as hydrocarbon ethers, e.g., tetrahydrofuran and the dimethylether of ethylene glycol; ketones such as methyl, isobutyl ketone and esters such as ethyl acetate and the like. Mixtures of organic solvents can also be used.

The components of the adhesive-forming composition of this invention can be mixed in any manner such as in bulk or in organic solvent. The MQ silsesquioxane resin is a solid and is conveniently prepared and handled in an organic solvent, the preparation of the composition of this invention preferably uses an organic solvent for the mixing of the MQ resin and siloxane gum. The mixing of the components can be accomplished by any of the techniques known in the art, such as milling, blending, stirring, and the like, either in batch or in continuous process.

The adhesive-forming composition of this invention can be prepared, with or without the aid of solvent, by simply mixing the MQ resin, silicone gum, and catalyst together in the stated proportion. The order of mixing of the components is not critical.

Laminates of the Invention

The adhesive compositions described herein can be used as part of a laminate of the invention. As used herein, the term "laminate" refers to a composite structure that is formed by uniting superposed layers of one or more materials.

For example, laminates of the invention can include a backing material, such as, for example, a sheet or film, having an adhesive composition of the invention applied thereto. Suitable backing materials include, but are not limited to, polymeric films or sheets formed from polyethylene, polypropylene, polyester, polyimide and the like.

Any of the adhesive compositions described herein may be applied to the backing material to form the laminate of the invention, which advantageously provide good peel adhesion to various surfaces. For example, a suitable adhesive composition includes a silylated polyurethane prepolymer, said polyurethane prepolymer being obtained from the silylation of a polyurethane prepolymer derived from the reaction of at least one polybutadiene polyol with at least one polyisocyanate; and an additional adhesive component other than the silylated polyurethane prepolymer. The exemplary additional adhesive component includes polyurethane adhesive, acrylic-based adhesive, methacrylic-based adhesive, natural rubber adhesive, synthetic rubber adhesive, polyvinylacetate adhesive, urea-formaldehyde adhesive, phenol-formaldehyde adhesive, formaldehyde resin, natural gum adhesive, silicone elastomer based adhesive, and combinations thereof. In one embodiment, the adhesive composition is a cured composition.

Illustratively, the adhesive composition may also include a filler, a tackifier, a silane adhesion promoter, a plasticizer, a solvent, a thioxtropic agent, a U.V. stabilizer, an antioxidant, a curing catalyst, or any combination thereof.

The laminate may also contain a release liner that is removably attached to the cured adhesive composition. The release liner can be a material such as paper or a polymeric film such as polyethylene, polypropylene, polyester, polyimide and the like. The release liner may also contain a release coating, such as, for an example, a silicone release coating, applied thereto, to facilitate the removal of the liner from the laminate.

In another embodiment, a laminate can be made by a method of providing an adhesive composition of the invention, applying the adhesive composition to the backing material, and curing the adhesive composition to provide an adhesive layer, thereby making the laminate.

In yet another embodiment, a laminate can be applied to a surface of a substrate by a method including providing a laminate having a backing material with a layer of an adhesive composition applied thereto and a release liner disposed on the layer of adhesive composition, removing the release liner, and applying the laminate to the surface of the substrate such that the layer of adhesive composition of the laminate contacts and adheres to the surface of the substrate.

The types of substrates in which the laminate of the invention can be applied include, but are not limited to, metal, plastic, wood, paper, cardboard, masonry, and glass.

The laminate of the invention is advantageously applied to substrates including surfaces of aircraft components, motor vehicles, buildings, machinery, various types of equipment or tools, and can advantageously be used for labeling, or masking areas to be protected from surrounding chemicals or environmental conditions.

FIG. 1 depicts an illustrative, non-limiting example of a laminate 10 of the invention. An adhesive composition is formed as coating 12 on backing sheet 11. The coated composition 12 is then cured to provide an adhesive to the backing sheet 11. A release liner 14 having a release coating 13 optionally can be applied to the cured coating 12. The release liner 14 with release coating 13 can be removed prior to applying the laminate 10 to a substrate.

Curing can be accomplished by exposure to moisture, such as atmospheric moisture. Typical curing conditions include room temperature curing at ambient temperature, e.g., about 23° C., and 50% relative humidity for 3 days and 37° C. and 95% relative humidity for another 4 days. Alternatively, elevated temperature curing can be effected. For example, water can be mixed with an appropriate solvent such as isopropanol followed by mixing with the adhesive composition, which can then be applied as a coating, and cured in conventional adhesive cure ovens known in the art.

According to another embodiment of the present invention, a transdermal drug delivery device is characterized by the use of the adhesive-forming composition of the present invention. The drug for this embodiment of the present invention can be any transdermally absorbable pharmaceutical, e.g., any of those referred to in U.S. Pat. Nos. 6,746,689, 6,858,997, 6,562,363, 5,556,636, 5,660,178 and 4,470,962 the entire contents of which are incorporated herein by reference.

In one embodiment of the invention, a transdermal drug delivery device contains a backing material on which the adhesive-forming composition of the present invention can be applied using methods well known to those skilled in the art. The backing material is preferably a flexible film that prevents bulk fluid flow and is inert to the ingredients of the adhesive-forming composition. In the case of adhesive-forming composition that contains a drug intended to be delivered across the skin surface and intended to have systemic action, the backing is preferably substantially resistant to the migration of the drug therethrough. The backing material can be any of the conventional materials used as backing for tapes or dressings, such as polyethylene, polypropylene, ethylene-vinyl acetate copolymer, ethylene propylene diene copolymer, polyurethane, rayon, and the like. Non-woven materials such as polyesters, polyolefins, and polyamides can also be used. Also, a layer of a hydrophobic elastomer such as polyisobutylene can function as a backing, as well as other known and convention materials in the art.

Non-limiting examples of pharmaceutical compounds include antibiotics such as penicillins, cephalosporins, erythromycins, tetracyclines, macrolides, aminoglycosides, fosfomycins and rifampicins; antipyretics, analgesics and anti-inflammatory drugs such as mefenamic acid, flufenamic acid, indometacin, diclofenac, acetaminophen, alclofenac, oxyphenbutazone, phenylbutazone, ibuprofen, ketoprofen, salicylic acid, methyl salicylate, L-menthol, camphor, sulindac, naproxen, fenbufen, aspirin, sulpyrine, tiaramide hydrochloride and piroxicam; antihistaminics such as alpha-chlorpheniramine maleate, diphenylpyraline, diphenhydramine, clemastine fumarate and promethazine hydrochloride; psychotropic drugs for hypnosis, sedation and ataraxia such as diazepam, chlorpromazine hydrochloride, chlordiazepoxide, sulpiride, haloperidol, ethyl loflazepate, fluphenazine, thioridazine, fludiazepam, flunitrazepam, phenobarbital, amobarbital, cyclobarbital, triazolam and nitrazepam; coronary vasodilators such as nitroglycerin, isosorbide dinitrate, nitroglycol, erythritol tetranitrate, pentaerythritol tetranitrate, verapamyl (hydrochloride), nifedipine, dipyridamole and diltiazem hydrochloride; antiarrhythmics and antihypertensive drugs such as propranolol (hydrochloride), pindolol, clonidine (hydrochloride), bupranolol, indenolol, nilvadipine, nipradilol, bucumolol, hydrazinc hydrochloride, ace-inhibitors, calcium channel blockers and the like; hypotensive diuretics such as hydrothiazide, benzylhydrochlorothiazide and cyclopenthiazide and diuretics such as furosemide, mefruside, trichlormethiazide and thiobromine; chemotherapeutic drugs such as aciclovir, nalidixic acid and sulfa drugs; anticancer agents such as 5-FU, vincristine, adriamycin, bleomycin, mitomycin, cisplatin and therarubicin; antiemetics agents such as metoclopramide, clebopride, scopolamine (hydrobromide) and domperidone; vitamins such as vitamin A, vitamin E, vitamin K, ergocalciferol, cholecalciferol, octotiamine and riboflavin tetrabutyrate; antispasmodics such as nitrazepam, clonazepam, baclofen and meprobamate; antitussives such as dextromethorphane, terbutaline (sulfate), ephedrine (hydrochloride), salbutamol (hemisulfate), isoproterenol and trimetoquinol hydrochloride; cardiacs such as prenylamine lactate, digitoxin and digoxin; vaso-constrictors, e.g., epinephrine, ephedrine and the like; anesthetics such as lidocaine, benzocaine and ethyl-p-aminobenzoate; cerebrovascular improvers such as hydergine, ergot alkaloid and ifenprodil; antifungal drugs such as pentamycin, amphotericin B, pyrrolnitrin, clotrimazole, benzalkonium chloride, nitrofurazone, nystatin and acetosulfamine; steroids such as hydrocortisone, prednisolone, paramethasone, beclomethasone dipropionate, flumethasone, betamethasone, betamethasone valerate, dexamethasone, trianicinolone, triamcinolone acetonide, fluocinolone, fluocinolone acetonide, clobetasol propionate, progesterone, testosterone and estradiol; antiparkinsonism drugs such as L-dopa, bromocriptine mesilate, trihexyphenidyl hydrochloride, mazaticol hydrochloride and biperiden hydrochloride; and biologics such as TRH, LHRH, TNF, lymphotoxin, interferon, urokinase, insulin, calcitonin, their derivative polypeptides and prostaglandins. Others such as tolbutamide and other antidiabetic drugs, colchicine and other anti-gout drugs and nicotine and other smoking suppressors.

The backing with an adhesive-forming composition applied thereto can be made into a patch with a backing by die-cutting individual patches from the sheet. Transdermal drug patches are known in the art, e.g. those referred to in U.S. Pat. No. 4,668,232. Alternatively, a patch with no backing can be prepared by die-cutting individual patches from a coated release liner prepared by methods know in the art or by die-cutting from a sheet of bioadhesive composition prepared by pressing between two sheets of release liner. A patch can be of any suitable size and shape, e.g., a 1 cm² circular disk.

In one embodiment of the invention, a drug is incorporated into the adhesive-forming composition of the invention. The drug is preferably present in an effective amount, which will depend upon the particular drug used, the intended therapy, and the desired duration of use of a particular individual application of the adhesive-forming composition containing the drug. Practical limitations on the amount of drug incorporated in a composition are that amount above which the composition begins to lose adhesion to a skin surface, and that amount below which a therapeutically effective blood level of drug cannot be achieved and/or maintained. In another embodiment of the invention, the drug can be present in a drug reservoir of the transdermal drug delivery device.

The adhesive-forming composition can contain other ingredients, for example excipients such as dyes, penetration enhancers, water-soluble or water-swellable fibrous reinforcers, and the like under circumstances and in amounts easily determined by those skilled in the art.

The adhesive-forming composition according to the invention exhibits excellent skin adhesion properties, even under the most difficult conditions. Furthermore, when the duration of application has terminated, e.g., removal of the transdermal drug delivery device provided with the adhesive-forming composition of the present invention, it can be removed from the skin without leaving any residues whatsoever. Compared to pressure sensitive adhesives made exclusively on the basis of polyacrylates or polyamine salts, a pressure sensitive adhesive of the present invention also has better release properties for the active substances dissolved or dispersed therein. A further advantage of the pressure sensitive adhesives prepared from the adhesive-forming composition according to the invention is that it is possible to add other pre-formed adhesives, e.g., polyacrylates, and others as disclosed in U.S. Pat. Nos. 6,936,661 and 5,750,136, the contents of which are incorporate herein by reference, which are already well known and commercially available in pharmaceutical technology and which are approved by the FDA.

The following examples are intended to illustrate, but in no way limit the scope of the present invention. All parts and percentages are by weight and all temperatures are in degrees Celsius unless explicitly stated otherwise.

EXAMPLE 1

Example 1 (Consists of Adhesives I and II and Illustrates Blending Silylated Polyurethane Adhesive with Conventional Non-Silicone Adhesives)

Adhesive I consisted of 25 g of adhesive of SPUR⁺ 200PSA prepared as follows: To a resin reaction vessel equipped with mixing capability, condenser, nitrogen atmosphere and heating was added 72.5 g of hydroxyl terminated polybutadiene Krasol®-LBH-P 2000 resin containing a hydroxyl number of 46, 145.0 g of hydroxyl terminated polybutadiene Krasol®-LBH-α 5000 resin containing a hydroxyl number of 21.7, 32.5 g of hydroxyl terminated polybutadiene Poly-bd® R20LM resin containing a hydroxyl number of 101 and 400.3 g of ethyl acetate. Refluxed for 2 hours to dry the mixture followed by cooling to 75-80° C. To this was added 0.27 g of a 10 wt % toluene solution of dimethylbis[(1-oxoneodecyl)oxy]stannane with agitation for 15 minutes. Next 18.6 g of isophorone diisocyanate was added for an NCO/OH equivalent ratio of 0.95. The reactants were heated at 75-80° C. until the wt % NCO was determined per standard methodology and found to be 0.0 wt % followed by drop wise addition of 1.34 g isocyanatopropyltrimethoxysilane. Heating was continued until wt % NCO was 0.0 wt % then cool to room temperature. The silylated polybutadiene polyurethane was diluted to 30 weight percent solids using 9.8 g ethyl acetate, 0.5 g water and one drop of a 10 weight percent dibutyltin bis(acetylacetonate) in toluene were thoroughly mixed. Adhesive II consisted of a 25 g of Aeroset® 1085-Z-38 (acrylic adhesive from Ashland Chemical) and 6.7 g ethyl acetate. Adhesives I and II were blended then bar coated to give a 25 micron adhesive thickness on 50 micron PET film, air dried 10 minutes then cured 30 minutes at 80° C. The blends were then tested after one week at room temperature. Peel adhesion per PSTC-101 was performed, except a glass panel rather than the standard stainless steel test panel was used. As indicated in Table 1, such adhesive blends can be prepared without altering significantly the peel adhesion properties.

TABLE 1

| Ratio of Adhesive I/II | Peel Adhesion, g/25 mm |
|---|---|
| 100/0 | 1311 |
| 75/25 | 1500 |
| 50/50 | 1028 |
| 0/100 | 1462 |

EXAMPLE 2

Example 2 (Consists of Adhesives I, II and III and Illustrates Blending Silylated Polyurethane Adhesive with Conventional Silicone Adhesives)

Adhesive I of Example 1 was prepared. Adhesive II consisted of 25 g of a high phenyl content silicone adhesive Silgrip® PSA6574 (a dimethyldiphenylsiloxane copolymers with MQ resin tackifier, available from Momentive Performance Materials-Silicones) and 10 g toluene. Adhesive III consisted of 25 g of a low phenyl content adhesive Silgrip® PSA950 (a dimethyldiphenylsiloxane copolymers with MQ resin tackifier, available from Ashland Chemical) and 10 g toluene. Adhesives I, II, and III were blended as presented in Table 2 below and then bar coated to give a 25 micron adhesive thickness on 50 micron PET film, air dried 10 minutes then cured 5 minutes at 150° C. These were then tested after one week at room temperature. Peel adhesion per PSTC-101 using standard stainless steel test panels was performed. Blending with silicone adhesives improved probe tack an indication of how well an adhesive wets out a surface without altering peel adhesion.

TABLE 2

| Ratio of I/II/III Adhesive Blends | Peel Adhesion, g/25 mm | Probe Tack, 100 g/cm$^2$ | Probe Tack, 1000 g/cm$^2$ |
| --- | --- | --- | --- |
| 100/0/0 | 1311 | 400 | 600 |
| 50/50/0 | 1461 | 1231 | 1359 |
| 50/0/50 | 1351 | 1120 | 1149 |

EXAMPLE 3

Example 3 (Consists of Adhesives I and II and Illustrates Blending with a Silylated Polybutadiene Polyurethane Pressure Sensitive Adhesive and a Polybutadiene Polyurethane)

Adhesive I consisted of 25 g of adhesive of SPUR$^+$ 2000PSA[1], a silylated polybutadiene polyurethane was diluted to 30 weight percent solids using 9.8 g ethyl acetate, 0.5 g water and one drop of a 10 weight percent dibutyltin bis(acetylacetonate) in toluene thoroughly mixed.

Adhesive II a non-silylated polybutadiene polyurethane was prepared as follows: To a resin reaction vessel equipped with mixing capability, condenser, nitrogen atmosphere and heating was added 72.5 g of hydroxyl terminated polybutadiene Krasol®-LBH-P 2000 resin containing a hydroxyl number of 46, 145.0 g of hydroxyl terminated polybutadiene Krasol®-LBH-P 5000 resin containing a hydroxyl number of 21.7, 32.5 g of hydroxyl terminated polybutadiene Poly-bd® R20LM resin containing a hydroxyl number of 101 and 333.2 g of ethyl acetate. Refluxed for 2 hours to dry the mixture followed by cooling to approximately 75° C. To this was added 0.27 g of a 10 wt % toluene solution of dimethylbis[(1-oxoneodecyl)oxy]stannane with agitation for 15 minutes. Next 18.5 g of isophorone diisocyanate was added for an NCO/OH equivalent ratio of 0.945. The reactants were heated at approximately 75° C. until the wt % NCO was determined per standard methodology and found to be 0.005 wt % then cooled to room temperature.

Coatings were prepared from blend ratios presented in Table 3, and bar coating 2 mil polyester film to yield an approximate 1.0 mil dry adhesive thickness. The adhesive was air-dried 10 minutes, followed by 2 minutes at 150° C. Peel adhesion per PSTC-101 using both stainless steel and glass panels were used. Table 3 below indicates such adhesive blends can be prepared without altering significantly the peel adhesion properties.

TABLE 3

| Ratio of Adhesive I/II | Peel Adhesion, Stainless Steel, g/25 mm | Peel Adhesion, Glass, g/25 mm | Probe Tack, 100 g/cm$^2$, g/cm$^2$ | Probe Tack, 1000 g/cm$^2$, g/cm$^2$ |
| --- | --- | --- | --- | --- |
| 100/0 | 551 | 330 | 433 | 415 |
| 80/20 | 1051 | 431 | 430 | 431 |
| 60/40 | 1278 | 856 | 472 | 505 |
| 40/60 | 1177 | 803 | 474 | 450 |
| 20/80 | 1713 | 1441 | 531 | 540 |

EXAMPLE 4

Example 4 (Consists of Adhesives I and II and Illustrates Blending with Silylated Polyurethane Adhesive and Conventional Silicone Adhesives with Peroxide Catalyst)

Adhesive I of Example 1 was prepared. Adhesive II consisted of 25 g of a low phenyl content adhesive Silgrip® PSA950 and 0.07 g benzoyl peroxide dissolved in 10 g toluene. Adhesives I and II were blended as presented in the Table 4 below then bar coated to give a 40 micron adhesive thickness on 50 micron PET film, air dried 10 minutes then cured 5 minutes at 150° C. The blends were tested after one week at room temperature. Peel adhesion per PSTC-101 using standard stainless steel test panels.

TABLE 4

| Ratio of I/II Adhesive Blends | Peel Adhesion, g/25 mm |
| --- | --- |
| 100/0 | 895 |
| 90/10 | 592 |
| 80/20 | 785 |
| 70/30 | 765 |
| 60/40 | 884 |
| 0/100 | 999 |

EXAMPLE 5

Example 5 (Consists of Adhesives I and II and Illustrates Blending with Two Silylated Polyurethane Adhesives of Different Compositions)

Adhesive I of Example 1 was prepared. Adhesive II consisted of a silylated polyester polyurethane and was prepared as follows: To a resin reaction vessel equipped with mixing capability, condenser, nitrogen atmosphere and heating was added 14.0 g of hydroxyl terminated poly(diethylene glycol glycerine adipate) resin containing a hydroxyl number of 90 with approximately 4.2 OH per molecule, 126.0 g poly(1,4-butanediol neopentyl glycol adipate) diol resin containing a hydroxyl number of 35, and 221.4 g of ethyl acetate. Refluxed for 2 hours to dry the mixture followed by cooling to approximately 75° C. To this was added 0.09 g of a 10 wt % toluene solution of dimethylbis[(1-oxoneodecyl)oxy]stannane with agitation for 15 minutes. Next 10.6 g of isophorone diisocyanate was added for an NCO/OH equivalent ratio of 0.93. The reactants were heated at approximately 75° C. until the wt % NCO was determined per standard methodology and found to be 0.00 wt % then 1.3 g isocyanatopropyltrimethoxysilane was added and heated until 0.00 wt % NCO determined.

Adhesives I and II were blended 50/50 w/w then bar coated to give a 40 micron adhesive thickness on 50 micron PET film, air dried 10 minutes then cured 2 minutes at 150° C.

These were then tested after one week at room temperature. Peel adhesion per PSTC-101 using standard stainless steel test panels the results of which are presented in Table 5.

TABLE 5

| Ratio of I/II Adhesive Blends | Peel Adhesion, g/25 mm |
|---|---|
| 100/0 | 895 |
| 50/50 | 1257 |
| 0/100 | 1349 |

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A laminate comprising a backing material having an adhesive layer adhered thereto, said adhesive layer being formed by curing a composition comprising:
   (a) a silylated polyurethane prepolymer, the silylated polyurethane prepolymer being obtained from the silylation of a polyurethane prepolymer derived from the reaction of at least one polybutadiene polyol with at least one polyisocyanate; and,
   (b) an additional adhesive component other than component (a),
   wherein the backing material comprises a polymer film formed from polyethylene, polypropylene, polyester or polyimide.

2. The laminate of claim 1 wherein the polybutadiene polyol possesses a number average molecular weight of from about 500 to about 10,000.

3. The laminate of claim 1 wherein the polybutadiene polyol possesses a number average molecular weight of from about 800 to about 5,000.

4. The laminate of claim 1 wherein the polybutadiene polyol possesses a primary hydroxyl group content of from about 0.1 to about 2.0 meq/g.

5. The laminate of claim 1 wherein the polyurethane prepolymer is silylated with at least one compound selected from the group consisting of aminosilane and isocyanatosilane.

6. The laminate of claim 5 wherein the aminosilane is of the general formula:

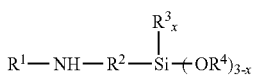

wherein $R^1$ is hydrogen or an alkyl group of from about 1 to about 10 carbon atoms, $R^2$ is a divalent alkylene group of from about 3 to about 10 carbon atoms, $R^3$ and $R^4$ each independently is an alkyl group of from about 1 to about 6 carbon atoms or an aryl group of from about 6 to about 8 carbon atoms, and x has a value of 0, 1 or 2 and the isocyanatosilane is of the general formula:

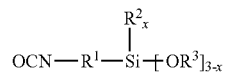

wherein $R^1$ is a divalent alkylene group of from about 3 to about 10 carbon atoms, $R^2$ and $R^3$ each independently is an alkyl group of from about 1 to about 6 carbon atoms or an aryl group of from about 6 to about 8 carbon atoms, and x has a value of 0, 1 or 2.

7. The laminate of claim 1 wherein the additional adhesive component (b) is at least one adhesive selected from the group consisting of polyurethane adhesive, acrylic-based adhesive, methacrylic-based adhesive, natural rubber adhesive, synthetic rubber adhesive, polyvinylacetate adhesive, urea-formaldehyde adhesive, phenol-formaldehyde adhesive, formaldehyde resin, natural gum adhesive, silicone elastomer based adhesive, and combinations thereof.

8. The laminate of claim 1 wherein the additional adhesive component (b) is a silylated polyurethane resin.

9. The laminate of claim 7 wherein the additional adhesive component (b) is selected from the group consisting of styrene butadiene rubber adhesive, styrene isoprene styrene based adhesive, isoprene-based adhesive, methyl, low phenyl and/or high phenyl silicone-based adhesive and combinations thereof.

10. The laminate of claim 1 wherein the adhesive composition further includes at least one additional component selected from the group consisting of filler, tackifier, silane adhesion promoter, plasticizer, solvent, thixotropic agent, U.V. stabilizer, antioxidant, curing catalyst, and combination thereof.

11. The laminate of claim 10 wherein the adhesive composition includes a MQ tackifier resin containing curing catalyst therefor.

12. An article having a surface to which the laminate of claim 1 is attached.

13. The article of claim 12 wherein said article is an aircraft.

14. A laminate comprising a backing material having an adhesive layer adhered thereto, said adhesive layer being formed by curing a composition comprising:
   (a) a silylated polyurethane prepolymer, the silylated polyurethane prepolymer being obtained from the silylation of a polyurethane prepolymer derived from the reaction of at least one polybutadiene polyol with at least one polyisocyanate; and,
   (b) an additional adhesive component other than component (a),
   wherein the laminate further includes a release liner.

15. The laminate of claim 14 wherein the release liner is fabricated from paper or a polymeric film formed from polyethylene, polyester or polyimide, and includes a release coating.

16. An article having a surface to which the laminate of claim 14 is attached.

17. A method for making a laminate comprising the steps of
   (a) providing an adhesive composition including: (i) a silylated polyurethane prepolymer, the silylated polyurethane prepolymer being obtained from the silylation of a polyurethane prepolymer derived from the reaction of at least one polybutadiene polyol with at least one polyisocyanate; and, (ii) an additional adhesive component other than component (i);

(b) applying said adhesive composition to a backing material; and (c) curing said adhesive composition to provide an adhesive layer, thereby making said laminate, wherein the backing material comprises a polymer film formed from polyethylene, polypropylene, polyester or polyimide.

18. A method for making a laminate comprising the steps of:

(a) providing an adhesive composition including: (i) a silylated polyurethane prepolymer, the silylated polyurethane prepolymer being obtained from the silylation of a polyurethane prepolymer derived from the reaction of at least one polybutadiene polyol with at least one polyisocyanate; and, an additional adhesive component other than component (i);

(b) applying said adhesive composition to a backing material; and (c) curing said adhesive composition to provide an adhesive layer, thereby making said laminate, wherein the method further comprises applying a release liner to the adhesive layer, said release liner being removable from the laminate.

19. A method of applying a laminate to a surface of a substrate comprising the steps of:

(a) providing a laminate comprising a backing material with a layer of a cured adhesive composition in contact with at least one side of the backing material, the laminate having a release liner disposed on the layer of the cured adhesive composition; the cured adhesive composition being prepared by curing an admixture of (i) a silylated polyurethane prepolymer, the silylated polyurethane prepolymer being obtained from the silylation of a polyurethane prepolymer derived from the reaction of at least one polybutadiene polyol with at least one polyisocyanate; and, (ii) an additional adhesive component other than component (i);

(b) removing the release liner;

(c) applying the laminate to the surface of the substrate such that the layer of adhesive composition of the laminate contacts and adheres to the surface of the substrate.

20. The method of claim 19 wherein the surface of the substrate comprises a surface of an aircraft component.

\* \* \* \* \*